United States Patent [19]

Bradford et al.

[11] Patent Number: Plant 7,431

[45] Date of Patent: Jan. 29, 1991

[54] PLUM-APRICOT HYBRID TREE (ROYAL VELVET PLUM-COT)

[76] Inventors: Norman G. Bradford, 11875 E. Savana Rd.; Lowell G. Bradford, 12439 E. Savana Rd., both of Le Grand, Calif. 95333

[21] Appl. No.: 458,570

[22] Filed: Dec. 28, 1989

[51] Int. Cl.[5] ..... A01H 5/00

[52] U.S. Cl. ..... Plt./38

[58] Field of Search ..... Plt./38

[56] References Cited

U.S. PATENT DOCUMENTS

P.P. 7,011 9/1989 Bradford ..... Plt. 38

*Primary Examiner*—James R. Feyrer

[57] ABSTRACT

The present invention relates to a plum-apricot hybrid tree and more particularly to a new and distinct variety broadly characterized by a dense, medium size, vigorous, tree that produces fruit that is similar to an apricot in skin appearance by having pubescence, but differs from a typical apricot by having a globose shape and by having a very dark purplish red skin color over its entire surface when mature. The fruit is of uniform medium size, has a sweetly delicious blend of both plum and apricot flavor, is firm for shipping, and matures under the ecological conditions described in late May, with first picking on May 19, 1989, making it an early ripening fruit compared with both plums and apricots. The variety was developed as the result of a seedling of an unknown plum as the seed parent and an unknown apricot as the per-chance pollen parent.

1 Drawing Sheet

BACKGROUND OF THE VARIETY

In a continuing effort to improve the quality of shipping fruits, we, the inventors, typically grow a large number of plum and apricot seedlings each year. Many of the plum seedlings are crossed with specifically selected pollen while the remainder of them are allowed to be randomly pollinated and are planted as a mixed group of varying seed parents. Most of these chance plum seedlings are cross-pollinated by other plums, but occasionally a few are crossed by an almond or an apricot. In 1984 we discovered the subject variety as such a plum-apricot hybrid tree among our plantings of randomly pollinated plum seedlings, thereby being a seedling of an unknown plum as the seed parent and an unknown apricot as the per-chance pollen parent. It was discovered in the cultivated area of our experimental orchard at Bradford Farms near Le Grand, Calif. in Merced County (San Joaquin Valley).

The present invention relates to a new and distinct variety of plum-apricot hybrid tree, which has been denominated varietally as "Royal Velvet Plum-Cot". The tree produces fruit that is medium in size, firm for shipping, early in ripening compared to typical plum and apricot varieties, a blend of both plum and apricot flavor, and somewhat similar to an apricot in external appearance by having typical apricot pubescence. The fruit is distinguished from typical apricots by being globose in shape and possessing full dark purple skin color at maturity.

The present variety most closely resembles the Red Velvet Plum-cot (U.S. Plant Pat. No. 7,011) by being self-sterile and by producing dark purplish red fruit that has skin pubescence, that is clingstone in type, and that is firm enough for commercial shipping, but is distinguished from the Red Velvet Plum-cot by having wood that is less brittle and by producing fruit that is globose in shape instead of oblong, that is much sweeter in flavor at shipping ripeness, that is more strongly attached to the stem, and that ripens 5 days later.

Subsequent to origination of the present variety of plum-apricot hybrid tree, we asexually reproduced it by budding and grafting, and such reproduction of plant and fruit characteristics were true to the original plant in all respects.

DRAWING

The accompanying photograph shows the characteristics of the whole fruit in skin color and form, a characteristic fruit divided on its suture plane showing the flesh and stone, and typical leaves.

POMOLOGICAL CHARACTERISTICS

Referring now more specifically to the pomological characteristics of this new and distinct variety of plum-apricot hybrid tree, the following has been observed under the ecological conditions prevailing near Le Grand, Merced County (San Joaquin Valley), Calif. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed.
Hardiness: Hardy.
Production: Medium productive.
Bearing: Uncertain bearer, not self-fruitful, and requires cross pollination by apricots.
Trunk:
- *Size.*—Medium.
- *Texture.*—Shaggy.
- *Color.*—Dark grayish reddish brown [47. d.gy.rBr].
- *Lenticels.*—Numerous. Color: Light grayish reddish brown [45. l.gy.rBr]. Average size: ¼" [6.4 mm.].

Branches:
- *Size.*—Medium.
- *Texture.*—Shaggy.

*Color.*—1st year wood — Topside: Light grayish red [18. l.gy.R]. 1st year wood — Underside: Strong yellow green [117. s.YG]. Older wood: Grayish reddish brown [46. gy.rBr]. Very newest growth: Grayish red [19. gy.R].

*Lenticels.*—Numerous, small.

Leaves:

*Size.*—Medium. Average length: 3" [76.2 mm.]. Average width: 2" [50.8 mm.].

*Thickness.*—Medium.

*Form.*—Oval.

*Apex.*—Aristate.

*Base.*—Rounded to slightly acute.

*Surface.*—Smooth.

*Color.*—Dorsal surface: Dark olive green [126. d.OlG]. Ventral surface: Moderate olive green [125. m.OlG].

*Margin.*—Finely crenate.

*Venation.*—Pinnately net veined.

*Petiole.*—Long and slender. Average length: 13/16" [20.6 mm.]. Average thickness: 1/16" [1.6 mm.]. Dorsal side color: Light grayish red [18. l.gy.R]. Ventral side color: Moderate yellow green [120. m.YG].

*Glands.*—Numbers: 1 to 4 per leaf. Position: Majority are oppositely positioned on petiole. Size: Medium. Form: Globose. Color: Light yellow green [119. l.YG].

*Stipules.*—Numerous. Average Length: 3/16" [4.8 mm.].

Flower buds:

*Hardiness.*—Tender.

*Size.*—Medium.

*Length.*—Medium.

*Form.*—Free.

*Surface.*—Pubescent.

Flowers:

*Blooming period.*—Early, compared to apricots and plums.

*Size.*—Medium.

*Color.*—White [263. White].

FRUIT

Maturity when described: Shipping ripe, May 24, 1989.

Date of first picking: May 19, 1989.

Date of last picking: May 26, 1989.

Size: Uniform, medium.

*Average diameter axially.*—1¾" [44.5 mm.].

*Average transversely in suture plane.*—2 1/16" [52.4 mm.].

Form: Uniform, symmetrical with respect to the suture, globose, and compressed in the axial direction.

*Longitudinal section form.*—Slightly oblate.

*Transverse section through diameter.*—Very round.

Suture: An inconspicuous line that extends from the base but discontinues at the apex.

Ventral surface: Rounded.

Lips: None.

Cavity: Flaring and circular with suture showing on one side only.

Base: Slightly truncate.

Apex: Rounded.

Pistil point: An inconspicuous dot slightly depressed within the suture.

Stem:

*Size.*—Medium.

*Average length.*—¼" [6.4 mm.].

*Average width.*—3/32" [2.4 mm.].

Skin:

*Thickness.*—Medium.

*Texture.*—Medium.

*Tenacity.*—Tenacious to flesh.

*Skin flavor.*—Astringent.

*Tendency to crack.*—None observed.

*Color.*—Dark purplish red [259. d.pR] over the entire surface.

*Down.*—Typical apricot pubescence, does not roll up when rubbed, scant.

Flesh:

*Color.*—Light orange yellow [70. l.OY] from skin to pit.

*Amygdalin.*—Scarce.

*Juice.*—Abundant.

*Texture.*—Medium, fine, crisp.

*Fibers.*—Abundant, fine, and tender.

*Ripens.*—Evenly, but slightly earlier at the apex.

*Flavor.*—Acidic and generously sweet.

*Aroma.*—Moderate.

*Eating quality.*—Excellent, even when only shipping ripe.

STONE

Type: Clingstone.

Form: Oval.

Base: Straight.

Apex: Mostly rounded.

Sides: Equal, flattened.

Surface: Typical apricot surface.

Ridges: Has a characteristic furrow along each side of the dorsal fin from base to apex.

Color: Moderate yellowish brown [77. m.yBr].

Thickness of pit wall: 1/16" [1.6 mm.].

Tendency to split: Slight.

Kernel:

*Form.*—Obovoid.

*Taste.*—Sweet.

*Viable.*—Yes.

*Average width.*—7/16" [11.1 mm.].

*Average length.*—9/16" [14.3 mm.].

Skin color: Pale yellow [89. p.Y].

Pellicle color: Dark grayish yellow [91. d.gyY].

Amygdalin: Scant.

USE

Market: Fresh market, both local and long distance shipping.

Keeping quality: Medium.

Shipping quality: Medium.

Resistance to insects: No unusual susceptibilities noted.

Resistance to diseases: Susceptible to blossom brown-rot.

Resistance to frost: Blossoms are very susceptible to frost.

Although the new variety of plum-apricot hybrid tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum-apricot hybrid tree, substantially as illustrated and described, that most closely resembles the Red Velvet Plum-cot (U.S. Plant Pat. No. 7,011) by being self-sterile and by producing dark purplish red fruit that has skin pubescence, that is clingstone in type, and that is firm enough for commercial shipping, but is distinguished therefrom and an improvement thereon by having wood that is less brittle and by producing fruit that is globose in shape instead of oblong, much sweeter in flavor at shipping ripeness, more strongly attached to the stem, and 5 days later in maturing.

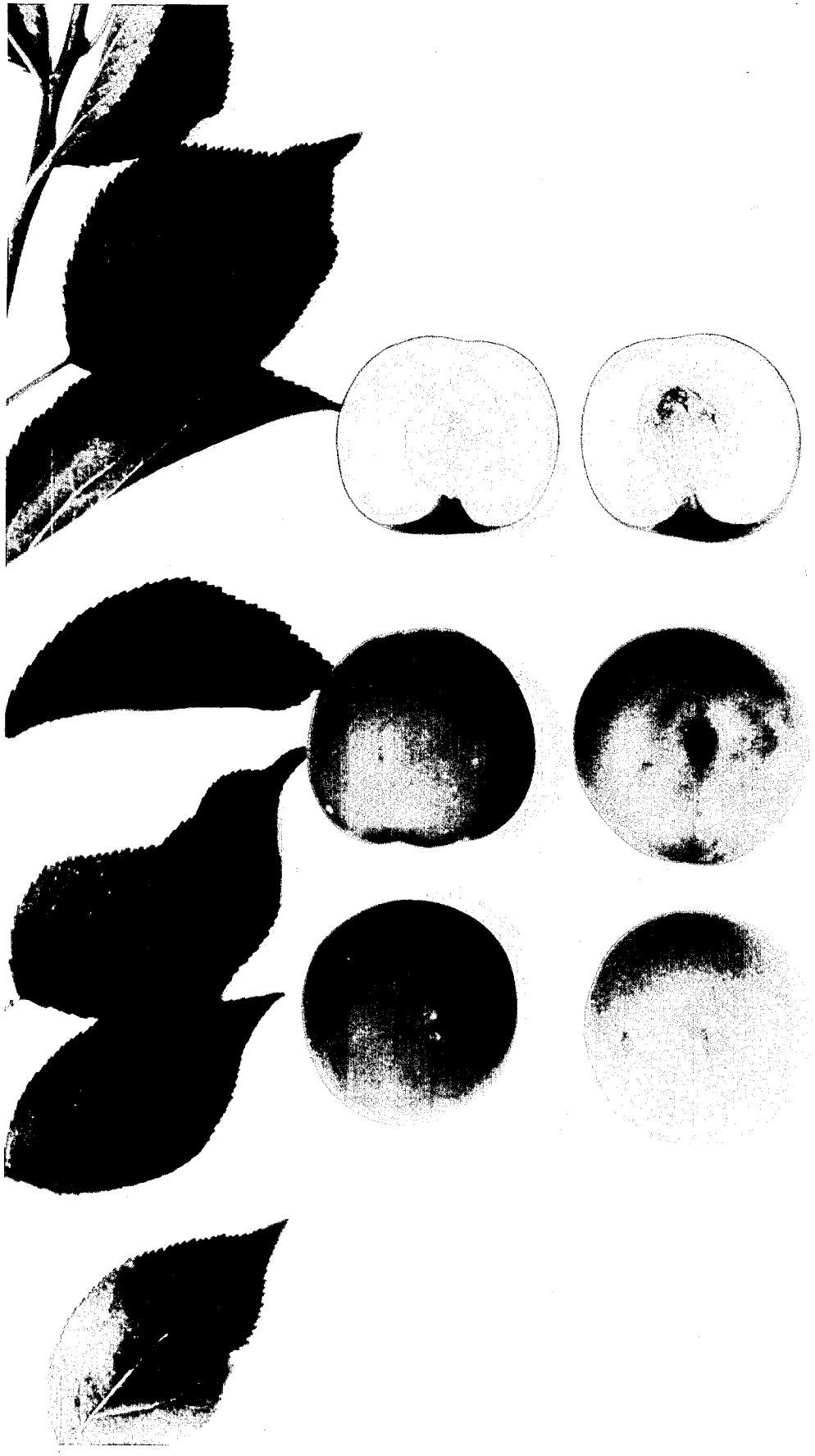

* * * * *